(12) United States Patent
Burk et al.

(10) Patent No.: US 6,249,129 B1
(45) Date of Patent: Jun. 19, 2001

(54) DEVICE FOR TRANSMISSION MEASUREMENT WITH THE AID OF MICROWAVES

(75) Inventors: Oliver Burk, Bad Liebenzell; Ulrich Klute, Neuenbuerg; Wilfried Reuter, Straubenhardt, all of (DE); Jean-Marie Weber, Altrirch (FR)

(73) Assignee: Berthold GmbH & Co. KG, Bad Wildbad (DE)

( * ) Notice: Subject to any disclaimer, the term of this patent is extended or adjusted under 35 U.S.C. 154(b) by 0 days.

(21) Appl. No.: 09/201,258

(22) Filed: Nov. 30, 1998

(30) Foreign Application Priority Data

Nov. 28, 1997 (DE) .......................................... 297 21 039 U

(51) Int. Cl.[7] .................................................. G01R 27/04
(52) U.S. Cl. .............................................................. 324/639
(58) Field of Search ...................................... 324/639, 640

(56) References Cited

U.S. PATENT DOCUMENTS

| | | | |
|---|---|---|---|
| 4,620,146 | * 10/1986 | Ishikawa et al. | ...................... 324/639 |
| 5,113,190 | 5/1992 | Klein et al. | . |
| 5,939,888 | * 8/1999 | Nelson | ................................ 324/639 |

FOREIGN PATENT DOCUMENTS

| | | |
|---|---|---|
| 1 210 998 | 2/1966 | (DE) . |
| 27 55 774 C2 | 7/1978 | (DE) . |
| 32 13 335 C2 | 10/1983 | (DE) . |
| 34 25 961 | 4/1985 | (DE) . |
| 296 17 488 | 6/1997 | (DE) . |
| 426 622 | 5/1991 | (EP) . |
| 515 831 | 12/1992 | (EP) . |
| 2 147 110 | 1/1985 | (GB) . |
| 90/01529 | 4/1991 | (WO) . |

* cited by examiner

Primary Examiner—Safet Metjahic
Assistant Examiner—J Kerveros
(74) Attorney, Agent, or Firm—Browdy and Neimark

(57) ABSTRACT

A system for transmission measurement with the aid of microwaves for the continuous determination of the concentration of a substance, the system being composed of: a transmission waveguide antenna for radiating microwave energy; a receiving waveguide a for receiving radiated microwave energy, each of the waveguides being provided with a window that is transparent to microwave radiation; and a signal processing circuit connected to the waveguides for supplying a microwave signal to the transmission waveguide antenna to cause the transmission waveguide antenna to radiate microwave energy via the window of the transmission waveguide antenna and for receiving from the receiving waveguide antenna a microwave signal created in the receiving waveguide antenna by microwave radiation received by the receiving waveguide antenna through the window in the receiving waveguide antenna.

15 Claims, 5 Drawing Sheets

DEVICE FOR TRANSMISSION MEASUREMENT WITH THE AID OF MICROWAVES

BACKGROUND OF THE INVENTION

1. Field of the Invention

The invention relates to a device, or system, for performing transmission measurements with the aid of microwaves for the continuous determination of the concentration of various types of solid or liquid substances including, but not limited to, syrup, or sugar juice, fertilizers, and fluids found in sewage treatment plants, milk processing and the paper industry, the device having two components which are introduced into the material to be measured and operate as a transmission and receiving antenna, respectively. For example, measurements of the concentration of sugar juice may be determined during a boiling step performed in a boiling apparatus in the course of a sugar crystallization process,

2. Prior Art

For many years microwave measuring processes have been regularly used in connection with the control of industrial processes. Typical applications include, for example, the determination of moisture in bulk materials and control of the fill level in large tanks and containers. Microwave measurement is also used for determining the density and concentration of solid and liquid materials to be measured. The transmission and reception of the microwaves takes place by means of so-called applicators, which are essentially used in connection with four methods: transmission methods, reflection methods, measuring of samples in a resonator, and the placement of the material to be measured as the terminal of a line. While the first two methods are mainly employed for on-line measurements, the last two are used for the testing of individual samples.

The determination of physical parameters, such as the density or concentration of materials to be measured in closed metal containers, for example, basically requires the insertion of the applicator into the container, for example by means of a flanged connection, so that a direct interaction of the electromagnetic waves with the material to be measured can take place. Furthermore, during on-line operation the determination of the measured value requires the continuous detection of a representative sample of the material to be measured by the microwaves.

The employment of microwave measuring methods for the determination of physical parameters, such as density, concentration, or moisture content of a material to be measured, has several advantages over conventional measuring methods, such as measurements of conductivity or capacitance. With increasing frequencies above 1 GHz, the interfering effects of, for example, ion conductivity in the measuring sample, or contacting problems, become more and more negligible. It is possible by means of modem strip conductor circuits to achieve very compact microwave modules, for example synthesizers, modulators or demodulators, with a large dynamic range in respect to attenuation of up to 80 dB, and phase-shift resolutions of up to a tenth of a degree.

If a dielectric is located in an alternating field, the dipoles can follow the field at sufficiently low frequencies. The electrical field and the polarization of the medium are in phase. If, with a further increase of the frequency, the dipoles can no longer follow the outer field, a phase shift between the polarization and the electrical field occurs. Losses occur because of this, which lead to heating of the sample, and the value of the dielectric constant (DC) becomes smaller (dispersion). A description of the relationship between the electric alternating field E and the polarization P is made possible by introducing the complex dielectric constant:

$$\in = \in' - j\in''.$$

Here, $\in'$ describes the proportion of P, which is in phase with field E and which for the frequency f=0 makes a transition into the static dielectric constant. $\in''$ describes the proportion of P which lags behind field E by 90°, and is therefore a measure for the dielectric losses.

This explanation suggests that in the microwave range a determination of the concentration can be based on the measurement of the real portion, $\in'$, as well as the imaginary portion, $\in''$, of the complex DC, or respectively of values, which are linked with these. Since the complex DC greatly depends on the physical properties of the material to be measured, for example the concentration, and on the selected high frequency, a frequency should be selected wherein the effect of the concentration to be measured on the resulting complex DC of the sample is as large as possible. To increase the measuring accuracy, the observed measured values can also be averaged over a larger frequency range.

A procedure for determining complex dielectric constant is described in Klein, A., "Ein Verfahren zur schnellen Bestimmung der nichtmagnetischer Materialien im Mikrowellenbereich" (A method for the rapid determination of the complex dielectric constant on non-magnetic materials in the microwave range), ARCHIV FÜR ELEKTRONIK UND UBERTRAGUNGSTECHNIK (Archive of electronics and transmission technology), Vol. 31 (1977) pp501–504.

Since two measurements, which are independent of each other, are required for determining $\in'$ and $\in''$, a complex transmission factor t is defined, which can be split into the magnitude T and the phase B. Here, t is defined as the ratio of the electric field strength of the wave $E_t$ transmitted through the sample and the electric field strength of the wave $E_j$ incident on the sample, as follows:

$$t = T \cdot e^{jB} = E_t / E_j$$

When determining the complex DC $\in$ from T and B it must be assured that the electromagnetic wave is sufficiently attenuated by the material to be measured, so that the reflections at the boundary transitions can become negligible.

The measuring process employed in the operation of a system according to the present invention is described in European Patent No. EP 0 515 831 A3, German Patent No. DE 34 25961 A1 and published UK Patent Application GB 2147110A, published May 1, 1985.

A device in accordance with the described type of transmission measurement with the aid of microwaves is disclosed in German Utility Model DE 296 17 488 U1, where two antennas, which are directly dipped into the medium to be measured are used with this "submerged sensor". Here, one antenna acts as the transmitting component, the other as the receiving component. Both antennas are designed as monopole radiators and are positioned at a suitable measuring location inside a boiling apparatus with the aid of an immersion tube. The control of the boiling process in evaporation crystallizers in the sugar industry is cited as a typical application of this solution. To this end, the antennas are installed in a boiling apparatus, and the concentration of the sugar syrup can be continuously determined during the progression of the boiling process by performing transmission measurements, such as has been basically described above.

Because of its specific structural characteristics, this already known solution has some serious disadvantages, notably in that a correct and precise measurement can be made only if definite marginal conditions and parameters are maintained.

The monopole radiators used in connection with the already known utility model have a very narrow bandwidth, which reduces the measuring accuracy since, for determining the measuring values for the phase shift and attenuation, it is not possible to measure over a larger frequency range (sweeping), which would increase accuracy.

Performing the measurement with the already known utility model with the two monopole antennas is essentially based on back-scattering of the microwaves because of the spherical characteristics of the radiation field of these monopole antennas. This results in very high intrinsic attenuation (attenuation without material to be measured), which limits the dynamic measuring range of the arrangement.

Positioning of the monopole antennas in the material to be measured (sugar juice/syrup) with the aid of the immersion tube requires the supply of high frequency energy by means of a coaxial line inside the immersion tube from the outer wall of the boiling apparatus to the two monopole antennas. The temperature dependency of these coaxial cables results in a considerable disadvantage, in that the temperature-dependent calibration of the arrangement must be strictly defined and monitored because of the large temperature variations in the boiling apparatus (approximately 75° C. during boiling and approximately 125° C. during evaporation). Thus, a relatively large expenditure is required here in order to prevent distortion of the results of the measurements.

BRIEF SUMMARY OF THE INVENTION

It is essentially an object of the invention to modify the already known technique in such a way that the parameters, which define the accuracy of the measurement, for example the fundamental attenuation, bandwidth, are considerably improved.

It is a further object of the invention to provide an improved microwave measurement device that that has reduced maintenance requirements, is structurally simpler and is less sensitive to exterior influences than known devices.

The above and other objects are achieved, in accordance with the invention, by a system for transmission measurement with the aid of microwaves for the continuous determination of the concentration of a substance, the system comprising: two waveguides having measuring portions which are immersed in the substance, the two waveguides comprising a transmission waveguide antenna for radiating microwave energy and a receiving waveguide antenna for receiving radiated microwave energy, each of the waveguides being provided with a window that is transparent to microwave radiation; and a signal processing circuit connected to the waveguides for supplying a microwave signal to the transmission waveguide antenna to cause the transmission waveguide antenna to radiate microwave energy via the window of the transmission waveguide antenna and for receiving from the receiving waveguide antenna a microwave signal created in the receiving waveguide antenna by microwave radiation received by the receiving waveguide antenna through the window in the receiving waveguide antenna.

The basic concept of the invention consists of the use of an interrupted waveguide with a very defined wave guidance and wave propagation. With a typical critical limit frequency of 2.5 GHz, such an arrangement has a very broad bandwidth, so that it is also possible, for determining the required measurement values (phase shift and attenuation), to perform sweep operations over an increased frequency range, which improve the accuracy of the results of the measurement. The waveguide solution also permits the coupling in of the microwaves outside of the material to be measured, so that the problems in connection with temperature-influenced line connections and the resultant calibration problems are avoided.

The arrangement with windows assures that the microwaves, which are directly transmitted from window to window, will be predominantly received and evaluated, which leads to a minimized intrinsic attenuation with an increase in the dynamic measuring range.

Thus, results of measurements with the system in accordance with the invention have already shown that in the determination of the sugar concentration there is no significant temperature dependency of this waveguide arrangement in the usual temperature range of the boiling apparatus. Comparative measurements with radiometric measuring methods, which have long been introduced in this field, show a high degree of agreement.

The attainment of the objects in accordance with the invention also permits the construction of essentially advantageous embodiments by means of which it is possible, for example, to optimize the adaptation to the respective material to be measured and the external parameters, such as the shape of the boiling apparatus and geometric marginal conditions.

A preferred exemplary embodiment of the system of the invention will now be described in greater detail with reference to the accompanying drawings.

DETAILED DESCRIPTION OF THE INVENTION

Figure 1:
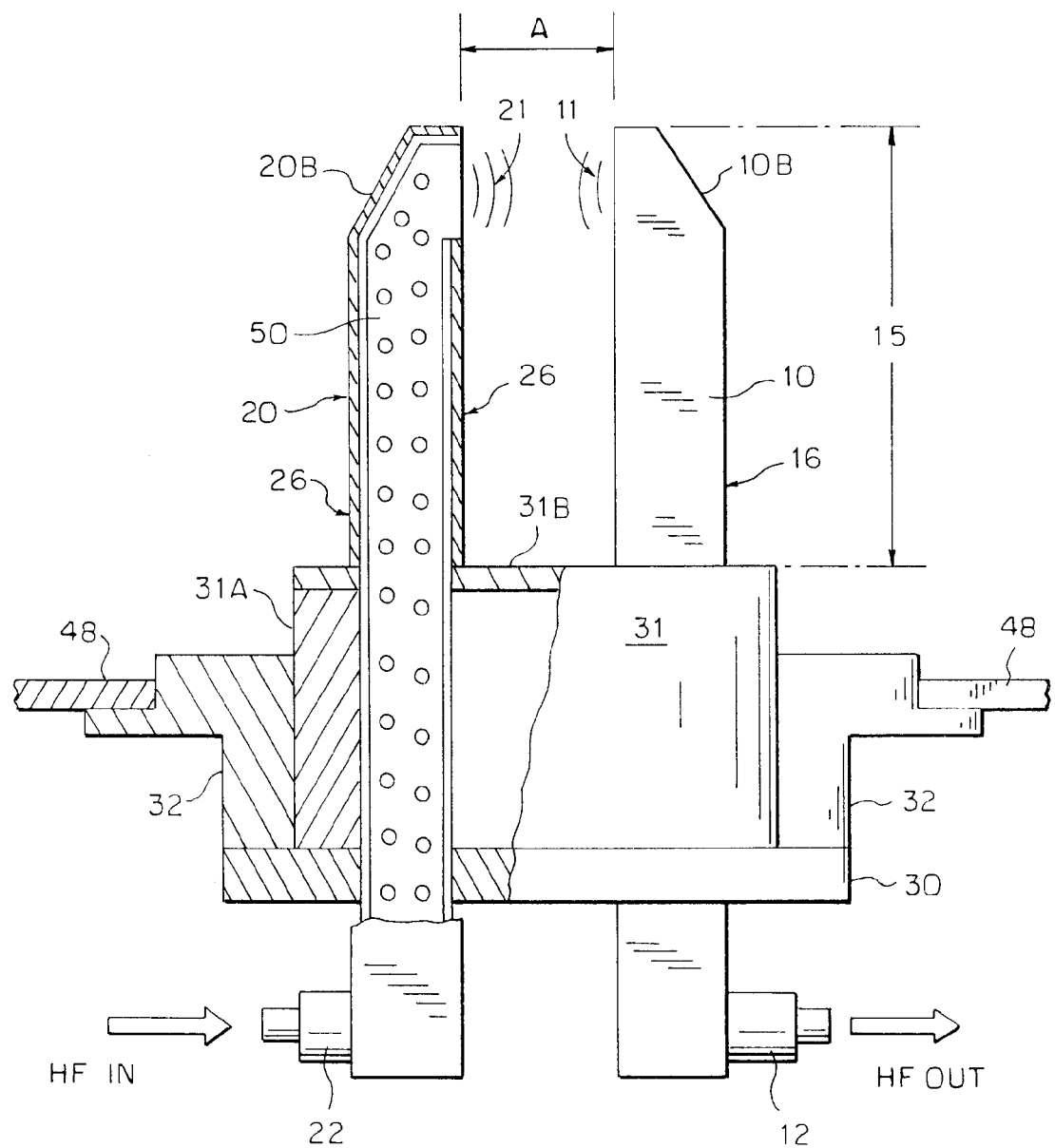
FIG. 1 is a plan view, partly in cross-section, of a preferred exemplary embodiment of a microwave measurement device in accordance with the invention.
Figure 2:
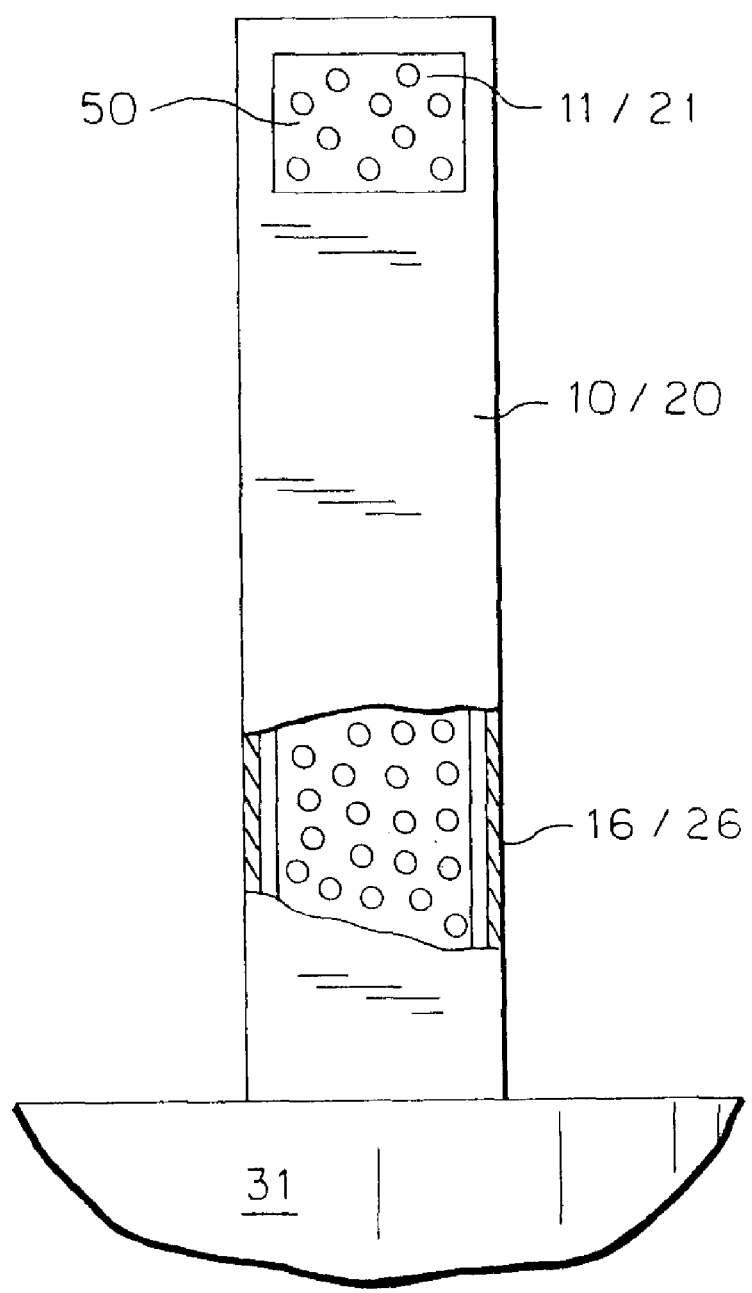
FIG. 2 is a front elevational view showing a lateral surface of one of the waveguides of FIG. 1.

The system shown in FIGS. 1 and 2 is composed of two mutually parallel round or square waveguides 10, 20 made of an electrically conductive material, such as special steel, which have been welded on the closure plate 30 of a cylindrical feed-through 31 also made of special steel. The closure plate 30 is carried by an annular flange 32, which in turn is seated in a recess in the wall or cover 48 of a boiling apparatus so that a section 15 of waveguides 10 and 20 project into the interior of the boiling apparatus. The special steel feed-through 31 consists of a cylinder jacket 31A with an upper closing cover 31B.

Round or square recesses have been cut into the upper closing cover 31B, in which the waveguides 10, 20 are sealingly maintained. The special steel feed-through 31 is therefore used for the secure holding and centering of the waveguides on the closure plate 30.

The illustrated device is disposed so that the material to be measured is located between waveguides 10 and 20, and more specifically between mutually facing surfaces of waveguides 10 and 20, which surfaces have windows, or cutouts, 11, 21 that are aligned with one another and through which microwaves exit and enter, as indicated in FIG. 2. Windows 11 and 21 are located at end areas of waveguides 10 and 20 in front of beveled portions 10B and 20B of waveguides 10 and 20. Feed-through plugs 12 and 22 for coupling high frequency electromagnetic energy in and out are located at the other end of the waveguides 10, 20 outside of the fastening flange 30. Depending on the geometric and physical measuring conditions, the waveguides can selectively be filled with a suitable dielectric 50. In addition, in section 15 immersed in the substance to be measured, the outer surfaces of waveguides 10 and 20 are completely covered with protective coatings 16, 26 which are compatible with foodstuff materials and whose wall thickness has been selected to be such that an optimal wave adaptation to the material to be measured is assured in the area of the exit and entry windows 11, 21.

The distance A between the waveguides and the windows is selected such that for the substance to be measured, the highest possible sensitivity in regard to the measuring value to be determined is achieved. The waveguide section 15 has been matched in such a way that, for one, the geometric conditions, such as internal heating coils in the container, for example, are taken into consideration, and also that as representative as possible a sample of the material to be measured is present between windows 10 and 20.

Figure 3:
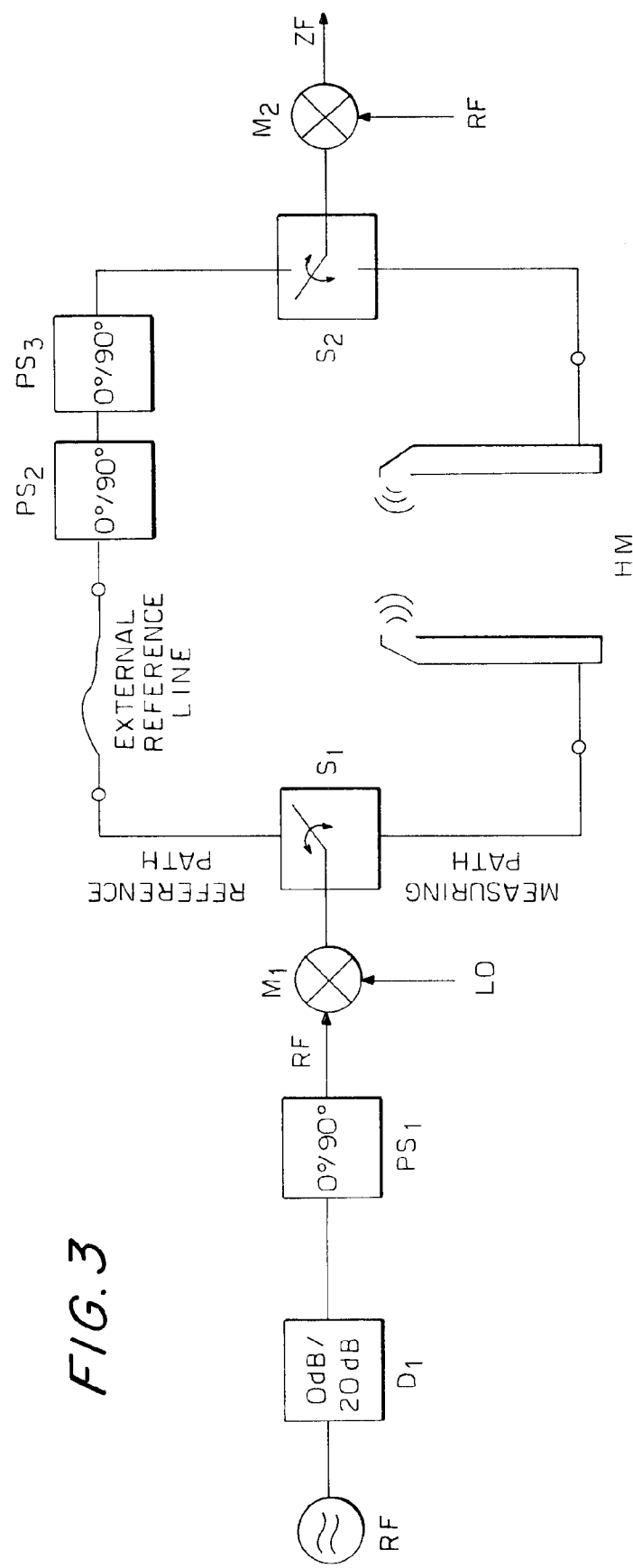
FIG. 3 is a block circuit diagram of a measuring arrangement using the system in accordance with the invention.

Waveguides 10 and 20 are connected as a measuring arrangement HM in a measuring circuit as shown in FIG. 3 for determining the complex transmission factor, and thus the attenuation and phase, which is a function of the properties of the material to be measured. A microwave frequency signal is generated by a synthesizer RF. This signal is composed of a series of pulses of microwave frequency cosine oscillations, the oscillations in each pulse have a respectively different frequency. The microwave frequencies of the cosine oscillations vary over a range of, for example, 2.7 to 3.4 GHz, with a constant difference existing between adjacent frequencies. A series of pulses may contain oscillations at, for example, 22 different frequencies. The signal generated by synthesizer RF is supplied to a mixer $M_1$ via a switchable attenuation member $D_1$ and a switchable phase shifter $PS_1$. Mixer $M_1$ additionally receives a 50 kHz square wave signal (LO) that amplitude modulates the microwave frequency signals supplied from synthesized RF. Mixer $M_1$ is followed by a switch $S_1$, which alternatively passes the mixed signal to a reference path and a measuring path that is connected to the waveguide measuring arrangement HM. The reference path contains two phase shifters $PS_1$ and $PS_2$. Both paths again come together at a second switch $S_2$, and from there the microwave signals are demodulated again in a further mixer $M_2$. The generated intermediate frequency ZF is digitized at a sampling rate of 100 kHz with the aid of an ADC (not shown). The reference path is used for calibration and for temperature compensation of the HF cables.

The measuring of the sample now takes place in that first a calibration measurement, for example with air as the medium between waveguides 10 and 20, is performed, and the measured phase and attenuation values are stored as reference values. Thereafter, the intermediate frequency is digitized in a predefined high frequency range at the 22 frequency points alternatively at phase shifts of zero degrees and 90 degrees. By means of this the real portion and the imaginary portion of the transmission factor are determined, wherein the amount of the complex value of attenuation and the angle between the complex value and the real separation axis corresponds to the phase shift. Averaging over the frequency support points is performed in that the arithmetic mean is formed during attenuation, and during the phase following a linear regression, the best fitting value at the position of the average frequency is selected as the phase shift. Then the phase shift and attenuation are the values to be determined for the sugar concentration of the material to be measured.

Figure 4:
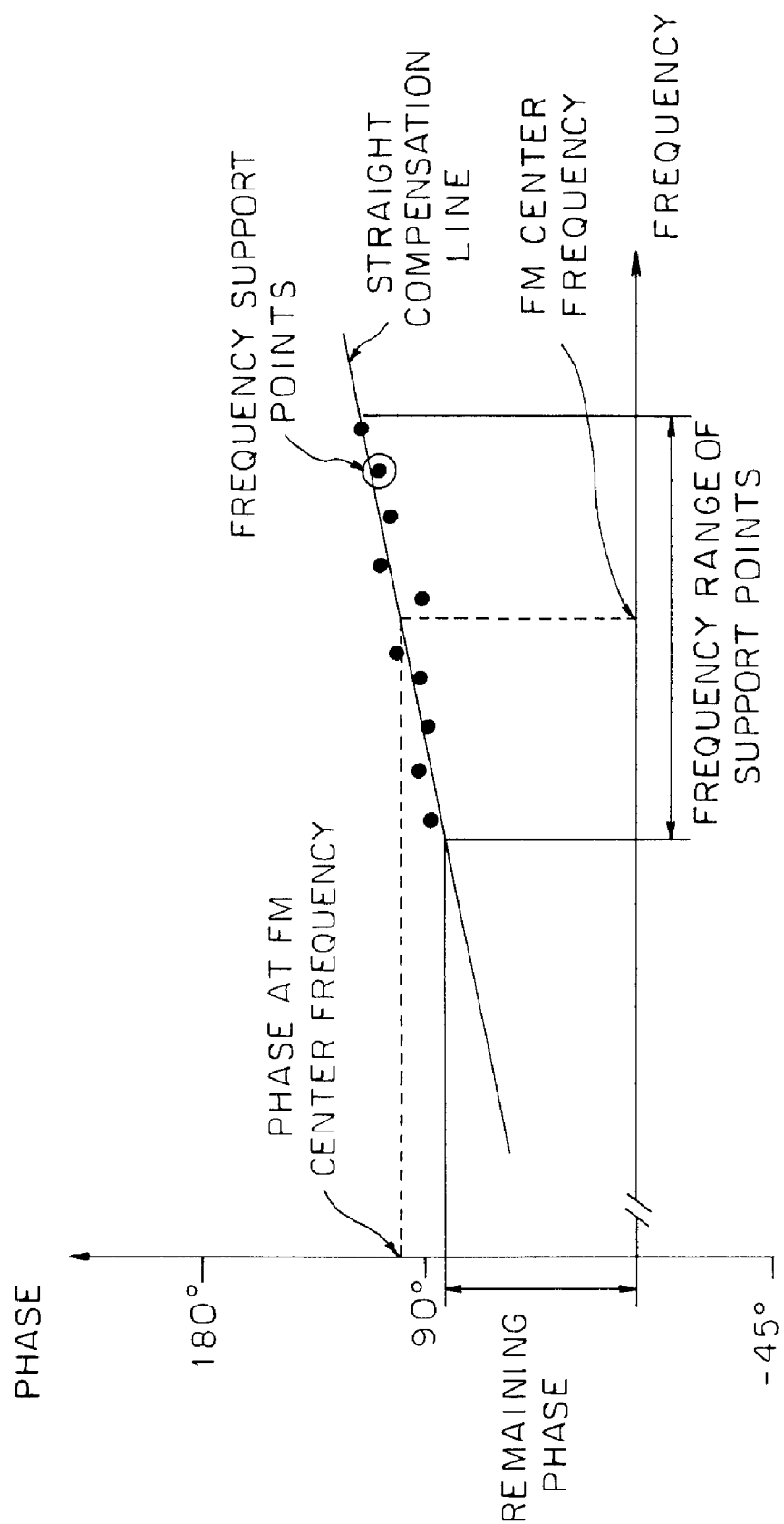
FIG. 4 is a diagram illustrating one facet of the measuring operation performed by the arrangement of FIG. 3.

Measured values for phase and attenuation are calculated in the manner disclosed in German Utility Model DE 297 21 039 UX, the contents of which are incorporated herein by reference, by averaging the individual measured values at the 22 frequency points, as illustrated in FIG. 4.

Conversion of the phase and attenuation values calculated from the measured values into substance concentration values can be performed according to the following equation:

$$\text{Concentration} = A1 \cdot \phi^2 + A2 \cdot \phi + B1 \cdot a^2 + B2 \cdot a + C$$

Where $\phi$ is phase,
  a is attenuation, and
  A1, A2, B1, B2 and C are coefficients resulting from assignment of microwave measuring values to the analyzed concentrations of measured substance samples.

Figures 5A, 5B:
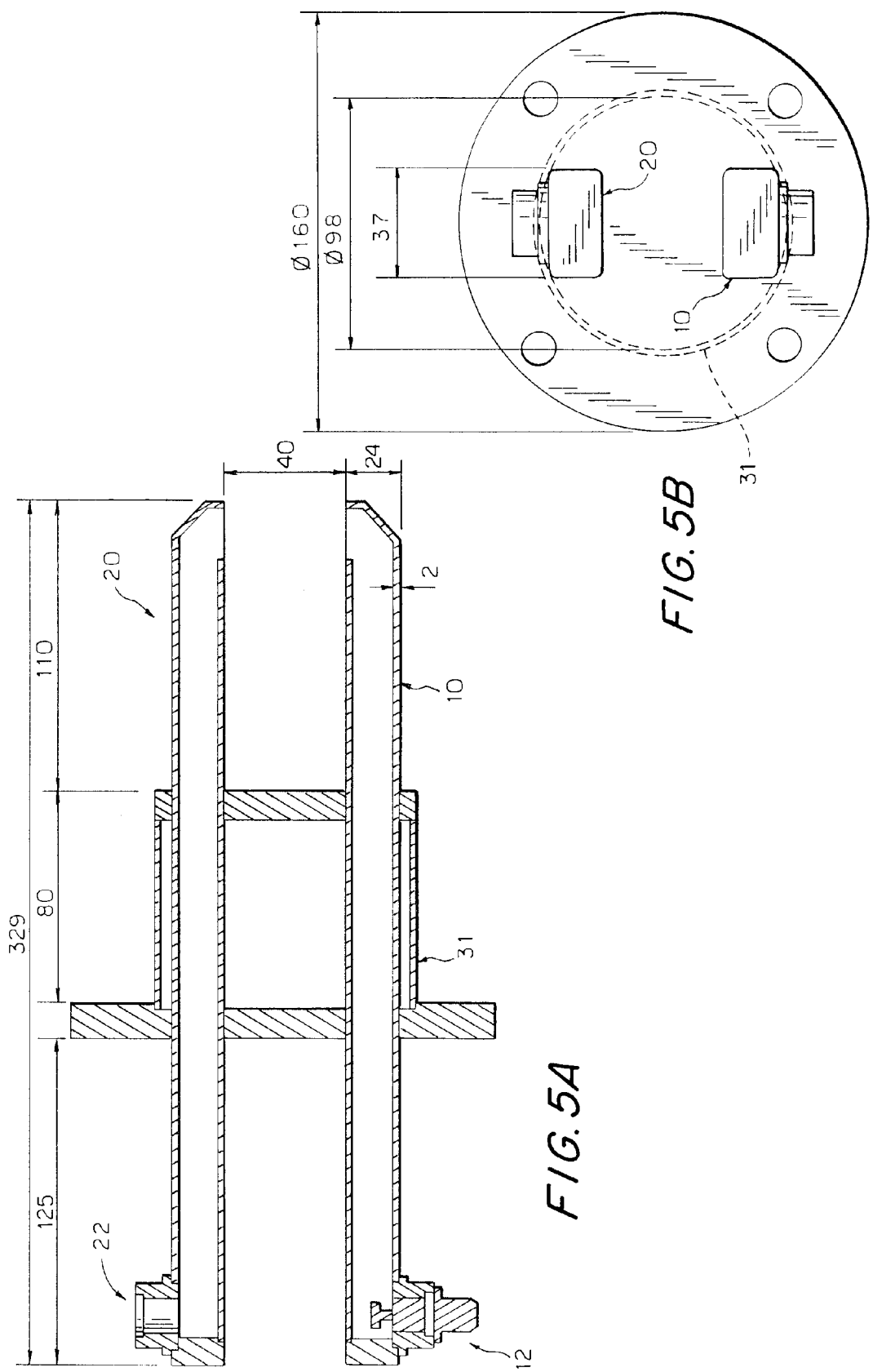
FIGS. 5A and 5B are, respectively, a side cross-sectional view and an end view of one practical embodiment of the measurement device shown in FIG. 1.

A practical embodiment of the arrangement of FIGS. 1 and 2 is shown in FIGS. 5A and 5B, which are drawn to scale and on which exemplary dimensions are shown in millimeters. All components are made of special steel, windows 11 and 21 measure 33×20 mm, windows 11 and 21 are spaced 40 mm apart, and each waveguide 10, 20 has exterior cross-sectional dimensions of 37×24 mm and interior cross-sectional dimensions of 33×20 mm. Feed-through 31 has a cylindrical shape with an interior diameter of 98 mm.

Each waveguide 10, 20 has beveled, or sloping, wall sections 10B, 20B which provide wave adaptation between the interior of the waveguides and the region between windows 11 and 21. Each waveguide may be filled with a suitable casting compound and each window 11, 21 may be covered with a PTFE sheet having a thickness of between 1 and 2 mm.

This application relates to subject matter disclosed in Germany in Application number 297 21 039.4, filed on Nov. 28, 1997, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A system for transmission measurement with the aid of microwaves for the continuous determination of the concentration of a substance, said system comprising: two waveguides having measuring portions which are immersed into the substance, said two waveguides comprising a transmission waveguide antenna for radiating microwave energy and a receiving waveguide antenna for receiving radiated microwave energy, each of said waveguides being provided with a window that is transparent to microwave radiation; and a signal processing circuit connected to said waveguides for supplying a microwave signal to said transmission waveguide antenna to cause said transmission waveguide antenna to radiate microwave energy via said window of said transmission waveguide antenna and for receiving from said receiving waveguide antenna a microwave signal created in said receiving waveguide antenna by microwave radiation received by said receiving waveguide antenna through said window in said receiving waveguide antenna.

2. The system in accordance with claim 1, wherein said measuring portion of each of said waveguides has a surface which contains a respective one of said windows and which faces the other one of said waveguides.

3. The system in accordance with claim 2, wherein said windows are aligned with one another.

4. The system in accordance with claim 3, wherein said measuring portion of each of said waveguides has an end area and said windows are located at said end areas.

5. The system in accordance with claim 4, wherein said end area of each of said waveguides has a beveled portion located behind, and aligned with, the respective window located at said end area.

6. The system in accordance with claim 1, wherein said waveguides are mounted on a boiler apparatus and have connecting portions that project out of the boiler apparatus, and said system further comprises microwave signal connectors connected to said portions of said waveguides.

7. The system in accordance with claim 1, wherein each of said waveguides has a square or circular cross section.

8. The system in accordance with claim 1, wherein said waveguides are made of an electrically conducting material.

9. The system in accordance with claim 8, wherein said waveguides are made of special steel.

10. The system in accordance with claim 1, wherein each of said waveguides is at least partially filled with a dielectric.

11. The system in accordance with claim 1, wherein said measuring portions of said waveguides have exterior surfaces covered with protective coatings having a thickness selected for optimizing the microwave adaptation to the substance in the area of said windows.

12. The system in accordance with claim 1, wherein said measuring portions have a length, said waveguides are spaced apart by a distance and said windows have a surface area, all of which are selected for optimizing the measuring sensitivity of said system.

13. The system in accordance with claim 1, wherein said waveguides have a cross section selected such that the transmission of microwaves in a frequency range between 1 and 12 GHz takes place in an essentially attenuation-free manner.

14. The system in accordance with claim 1, wherein each of said waveguides is a hollow waveguide of square or circular cross-section.

15. The system in accordance with claim 14 wherein each of said waveguides is at least partially filled with a dielectric.

* * * * *